| United States Patent [19] | [11] Patent Number: 4,786,426 |
|---|---|
| Gemmill, Jr. et al. | [45] Date of Patent: Nov. 22, 1988 |

[54] LUBRICANT COMPOSITION

[75] Inventors: Robert M. Gemmill, Jr., Pitman; Andrew G. Horodysky, Cherry Hill, both of N.J.

[73] Assignee: Mobil Oil Corporation, New York, N.Y.

[21] Appl. No.: 109,951

[22] Filed: Jan. 7, 1980

[51] Int. Cl.$^4$ .......................... C10M 1/54; C10M 1/10
[52] U.S. Cl. .................................... 252/49.6; 548/110
[58] Field of Search ....................... 252/49.6; 548/110

[56] References Cited

U.S. PATENT DOCUMENTS

| 2,372,409 | 3/1945 | Tryon | 548/239 |
|---|---|---|---|
| 2,504,951 | 4/1950 | Tryon | 548/239 |
| 2,759,894 | 8/1956 | Matuszak | 548/239 X |
| 2,993,765 | 7/1961 | Belden | 548/110 X |
| 3,030,375 | 4/1962 | De Gray et al. | 548/110 |
| 3,070,603 | 12/1962 | Belden | 548/110 |
| 3,256,310 | 6/1966 | Weil | 548/239 X |
| 3,654,229 | 4/1972 | Hoyt | 548/239 X |
| 4,097,389 | 6/1978 | Andress, Jr. | 252/49.6 X |
| 4,116,876 | 5/1978 | Brois et al. | 252/49.6 |
| 4,162,224 | 7/1979 | Bridger | 252/49.6 |

*Primary Examiner*—Robert V. Hines
*Attorney, Agent, or Firm*—Alexander J. McKillop; Michael G. Gilman; Van D. Harrison, Jr.

[57] ABSTRACT

A borated oxazoline monoester, made by reacting a boron compound with the product of reaction between tris(hydroxymethyl)aminomethane and carboxylic acid is a new composition of matter. It is useful in a lubricating oil for reducing friction, and, therefore, fuel consumption in an internal combustion engine.

12 Claims, No Drawings

LUBRICANT COMPOSITION

BACKGROUND OF THE INVENTION

1. Field of the Invention

The invention is concerned with a lubricant composition. More particularly, it is concerned with a lubricant composition containing a friction reducing additive which when in a lubricating oil composition reduces friction in an internal combustion engine and thereby decreases the fuel consumption thereof.

2. Discussion of the Prior Art

The synthesis of hydrocarbyl oxazoline esters from the appropriate carboxylic acid and 2-amino-2-(hydroxymethyl)-1,3-propanediol is known. However, no art is known that teaches or suggests the use of the herein disclosed derivatives as friction reducing additives in automotive engine oils.

Over the years numerous efforts have been made to reduce the amount of fuel consumed by automobile engines and other lubricated devices. Many such efforts have been directed at mechanical means, as for example, setting the engine for a leaner burn or simply building smaller cars and smaller engines.

Other efforts have revolved around finding lubricants that reduce the overall friction in the engine and/or the power train components, thus allowing a reduction in energy requirements thereof. Much work has been done with mineral lubricating oils and greases, modifying them with additives to enhance their friction properties. On the other hand, new lubricants have been synthesized and compounded for use in modern engines. Many of these are lower viscosity fluids which result in a reduction of friction. With respect to some present synthetic lubricant formulations, it is the physical properties of the oil itself, such as viscosity characteristics, that provide improved lubrication and reduced fuel consumption, not the additives therein.

SUMMARY OF THE INVENTION

The invention provides a lubricant composition comprising a major proportion of a lubricant and a friction reducing amount of a borated hydrocarbyl oxazoline ester. The invention also provides a method of reducing fuel consumption of an internal combustion engine by lubricating the moving parts thereof with a lubricating oil containing said oxazoline ester. The hydrocarbyl group mentioned hereinabove has 9 to 49 carbon atoms. It is meant to include alkyl, alkenyl, aryl, aralkyl and alkaryl, wherein the aryl portion has 6 to 14 carbon atoms.

DESCRIPTION OF SPECIFIC EMBODIMENTS

It has been estimated that if all the fuel burned in an automobile weighing somewhat over 4000 pounds and having a 10:1 compression ratio could be used to propel it, it could travel between 125 and 130 miles on a gallon of gasoline. This assumes a speed of around 40 mph.

The losses due to fuel pumping, tare, friction, and the like reduce the energy available for propelling the car to about 13.1%.

Of this loss, approximately 5%, or 6.4 mpg, can be accounted for by losses due to lubricated engine components. Consequently, a mere 10% decrease in boundary and viscous friction would lead to a 3.8% increase in fuel economy (from 16.7 mpg to 17.3 mpg). It is little wonder, then, that energy companies are concerned with finding new lubricants or new additives that have superior lubricity properties.

As was mentioned hereinabove, one method of boosting fuel economy is to optimize the lubrication of the engine and drive train; that is, minimize friction losses between lubricated moving parts. The benefit using certain synthetic lubricating oils over high grade mineral lubricating oils can be better than 4%, attained solely by lowering the *viscous* friction of the engine lubricant. Additional improvements may be realized by modifications of the boundary friction of the lubricant.

Broadly, the products useful in this invention can be made by methods well known in the prior art. For example, they are made under appropriate conditions by reacting a hydrocarbyl carboxylic acid with 2-amino-2-(hydroxymethyl)-1,3-propanediol also called tris(hydroxymethyl)aminomethane, to obtain the oxazoline ester, followed by reaction of such ester with a boron compound, such as boric acid.

The following illustrates the reaction with boric acid and 1-3 moles of the oxazoline ester

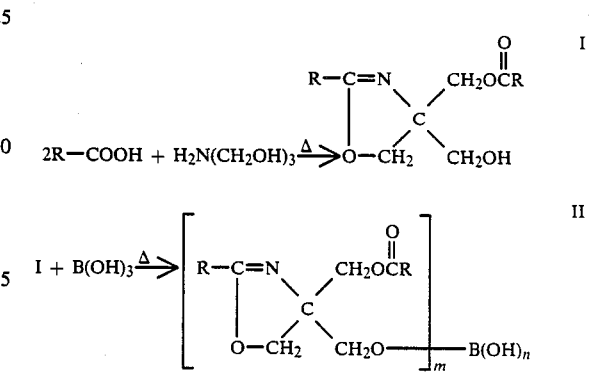

wherein R is the same or different hydrocarbyl group having 9 to 49 carbon atoms, m is 1 to 3 and n is 0 to 2.

Other boron compounds may also be used. These include the alkyl borates of the formula $(R'O)_x B(OH)_y$ wherein $R'$ is a $C_1$–$C_6$ alkyl group, x is 1 to 3 and y is 0 to 2. When this reactant is used, the final product can be illustrated by compound II, where m is 3 and n is 0, when three moles of compound I are reacted with one mole of the boron compound and the reaction is carried to completion. However, when less than a stoichiometric amount of oxazoline is present for reaction, the boron will still have attached thereto one or more —OR groups or one or more —OH groups, depending upon which of such groups react. That is to say, if $R'OB(OH)_2$ is used, the product may be

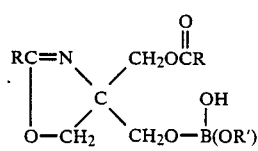

if the —OH reacts or

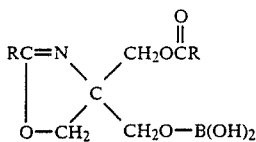

if the —OR' reacts.

The carboxylic acid, as indicated may have from 10 to 50 carbon atoms, including the carboxyl carbon atom. These include the saturated decanoic, dodecanoic, tetradecanoic, octadecanoic, eicosanoic acids and the like, as well as the unsaturated acids, including particularly oleic acid.

The first reaction, i.e. between the monocarboxylic acid and the amine, can be carried out at from about 80° C. to about 250° C., preferably from about 120° C. to about 190° C. The temperature chosen will depend for the most part on the reactants chosen and whether or not a solvent is used. In carrying out this reaction, it is essential that quantities of reactants be chosen such that at least one hydroxyl remains for the reaction with the boron compound. For example, in the reaction illustrated, two moles of the acid and one mole of the amine are required. An excess of acid in this case would lead to the formation of some diester oxazoline, in addition to the preferred oxazoline monoester.

In carrying out the reaction to form the boron product, up to stoichiometric amounts of the oxazoline ester and boron compound may be used, i.e. for every one mole of boron compound use from 1 to 3 moles of oxazoline monoester. The temperature of reaction can vary over the range of from about 75° C. to about 250° C., preferably about 100° C. to about 200° C.

While atmospheric pressure is generally preferred, the reaction with the boron compound can be advantageously run at from about 0.3 to about 2 atmospheres. Furthermore, a solvent is desirable. In general, any polar or nonpolar, unreactive solvent can be used, including toluene, xylene, 1,4-dioxane and butanol-1.

The times for the reactions are not critical. Thus, any phase of the process can be carried out in from 1 to 8 hours.

The additive may be used effectively to impart to organic media, particularly to greases and lubricating oils, the properties mentioned hereinabove. An effective amount of the additive compound will range from about 0.1% to about 10% by weight. Preferably the organic medium or substrate, e.g., oil of lubricating viscosity or grease therefrom, contains from about 1.0% to 5.0% of the additive and more preferably from about 2.0% to about 4.0% by weight thereof, based on the total weight of the lubricant composition.

Of particular significance, in accordance with the present invention, is the ability to improve the resistance to oxidation and corrosion of oleaginous materials such as lubricating media which may comprise liquid oils, in the form of either a mineral oil or a synthetic oil, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SUS at 100° F. to about 600 SUS at 100° F., and preferably, from about 50 to about 250 SUS at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent and other additive components to be included in the grease formulation. A wide variety of materials may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. These synthetic oils may be used alone, in combination with mineral oils, or with each other as a lubricating oil. Typical synthetic vehicles include synthetic hydrocarbons such as polyisobutylene, polybutenes, hydrogenated polydecenes, the polyglycols, including polypropylene glycol, polyethylene glycol, synthetic ester oils illustrated by trimethylolpropane esters, neopentyl alcohol and pentaerythritol esters, di(2-ethylhexyl)sebacate, di(2-ethylhexyl)adipate, dibutyl phthalate and other types, as for example, fluorocarbons, esters of phosphorus-containing acids, liquid ureas, ferrocene derivatives, hydrogenated synthetic oils, chain-type poly-phenols, siloxanes and silicones (polysiloxanes), alkyl-substituted diphenyl esters typified by a butylsubstituted bis(p-phenoxyphenyl)ether and phenoxyphenyl ether.

Having described the invention broadly, the following are offered as specific illustrations. They are illustrations only, and the invention is not limited thereby.

EXAMPLE 1

(A) A 12 liter glass reactor fitted with a nitrogen inlet, stirrer, thermometer, Dean-Stark water trap and condenser was used for the reaction.

Oleic acid (20 moles, 5649 grams), 2-amino-2-(hydroxymethyl)-1,3-propanediol (10.0 moles, 1211.4 grams) and 1.0 liter of xylene were charged to the reactor.

The reaction mixture was heated, using a nitrogen purge and rapid stirring, to a maximum temperature of 195° C. for 20 hours. Water evolved over the temperature range of 125°–195° C. A total of 548 ml (theory—540 ml) of water was collected. The xylene was removed by vacuum distillation at 130° C. and approximately 5 mm Hg. The product was then vacuum filtered through HiFlo filter aid to yield a clear, amber, fluid filtrate which is mono(hydroxymethyl)oleyl oxazoline monooleate.

(B) The boration was performed in a 1 liter glass reactor fitted as described above. The oxazoline product (0.20 mole, 126.2 grams), boric acid (0.067 mole, 4.1 grams) and 1-butanol (0.54 mole, 40.0 grams) were charged to the reactor. The reaction mixture was heated for 10 hours at a maximum temperature of 173° C. A total of about 3.4 ml (3.6 ml theory) of water was collected. At the end of the reaction, the 1-butanol was removed by vacuum distillation. 90% of the 1-butanol (36.0 grams) was recovered. The final borated product was vacuum filtered through HiFlo filter aid to yield a clear, light amber, fluid product.

EXAMPLE 2

A 3 liter glass reactor fitted as in Example 1 was used.

(A) Myristic acid (4.0 moles, 913.5 grams), 2-amino-2-(hydroxymethyl)-1,3-propanediol (2.0 moles, 242.2 grams) and 550 ml of toluene were charged to the reactor.

The reaction mixture was heated to a maximum temperature of 172° C. for 20 hours. A total of 108 ml of water (theory=108 ml) was collected. The toluene solvent was removed by vacuum distillation and the hot product was vacuum filtered through HiFlo filter aid. The oxazoline product became a crystalline solid at room temperature.

(B) The boration reaction was performed without the presence of 1-butanol. The above oxazoline product (1.72 moles, 900.0 grams), boric acid (0.58 mole, 35.8 grams) and 300 ml of toluene were charged to the above reactor.

The reaction mixture was heated to a maximum temperature of 190° C. for 10 hours. A total of 30.5 ml of water (theory=31 ml) was collected. The toluene was removed by vacuum distillation and the hot reaction product was vacuum filtered through HiFlo filter aid. The borated product was a low melting, waxy solid at room temperature and was moderately soluble in the test oil.

Data showing the friction reducing properties were determined in the Low Velocity Friction Apparatus (LVFA), as follows.

Description

The low Velocity Friction Apparatus (LVFA) is used to measure the coefficient of friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.2). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam-motor arrangement.

Procedure

The rubbing surfaces and 12-13 ml of test lubricants are placed on the LVFA. A 240 psi load is applied, and the sliding speed it maintained at 40 fpm at ambient temperature for a few minutes. A plot of coefficients of friction (Uk) over the range of sliding speeds, 5 to 40 fpm (25-195 rpm), is obtained, A minimum of three measurements is obtained from each test lubricant. Then, the test lubricant and specimens are heated to 250° F., another set of measurements is obtained, and the system is run for 50 min. at 250° F., 240 psi, and 40 fpm sliding speed. Afterward, measurements of Uk vs speed were taken at 240, 300, 400 and 500 psi. Freshly polished steel specimens are used for each run. The surface of the steel is parallel ground to 4 to 8 micro-inches. The results in Table 1 were at 250° F. and 500 psi.

The borated oxazoline esters were evaluated at 4% concentration by weight of lubricating oil in a fully formulated 5W-20 synthetic lubricating oil comprising an additive package including antioxidant, detergent and dispersant. The data in Table 1 are reported as percent reduction in coefficent of friction at two speeds.

TABLE 1

| | EVALUATION OF FRICTION REDUCTION | | |
|---|---|---|---|
| | Additive conc., wt. % | Friction Reduction, % at Sliding speeds | |
| Composition | in test oil | 5 ft/min | 30 ft/min |
| Oil only | 0 | 0 | 0 |
| Example 1(A) | 4 | 19 | 11 |
| Example 1(B) | 4 | 39 | 24 |
| Example 2(B) | 4 | 42 | 32 |

We claim:

1. A compound of the formula:

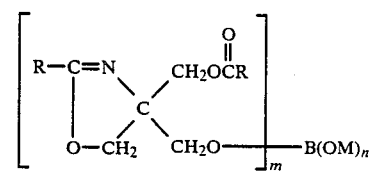

wherein R is the same or different hydrocarbyl having 9 to 49 carbon atoms, m is 1 to 3, n is 0 to 2 and M is H or R', R' being an alkyl containing 1 to 6 carbon atoms.

2. The compound of claim 1 wherein R is derived from oleic acid.

3. The compound of claim 1 wherein B is derived from boric acid, m is 3 and n is zero.

4. The compound of claim 1 wherein B is derived from $(R'O)_xB(OH)_y$ wherein R' is a $C_1$-$C_6$ alkyl group, x is 1 to 3 and y is 0 to 2.

5. A lubricant composition comprising a major proportion of a lubricant and a friction reducing amount of a compound of the formula:

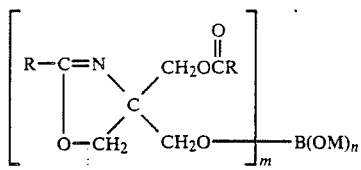

wherein R is the same or different hydrocarbyl having 9 to 49 carbon atoms, m is 1 to 3, n is 0 to 2 and M is H or R', R' being an alkyl containing 1 to 6 carbon atoms.

6. The composition of claim 5 wherein R is derived from oleic acid.

7. The composition of claim 5 wherein B is derived from boric acid, m is 3 and n is zero.

8. The composition of claim 5 wherein B is derived from $(R'O)_xB(OH)_y$ wherein R' is a $C_1-C_6$ alkyl group, x is 1 to 3 and y is 0 to 2.

9. A method of reducing fuel consumption in an internal combustion engine comprising lubricating said engine with a lubricant composition comprising a lubricating oil and a fuel consumption reducing amount of a compound of the formula

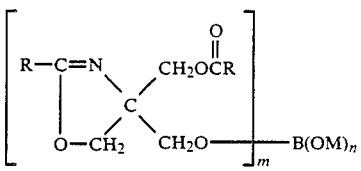

wherein R is the same or different hydrocarbyl having 9 to 49 carbon atoms, m is 1 to 3, n is 0 to 2 and M is H or R', R' being an alkyl containing 1 to 6 carbon atoms.

10. The method of claim 9 wherein said compound R is derived from oleic acid.

11. The method of claim 9 wherein in said compound B is derived from boric acid, m is 3 and n is zero.

12. The method of claim 9 wherein in said compound B is derived from $(R'O)_xB(OH)_y$ wherein R' is a $C_1-C_6$ alkyl group, x is 1 to 3 and y is 0 to 2.

* * * * *